(12) United States Patent
Pyle et al.

(10) Patent No.: US 6,925,889 B2
(45) Date of Patent: Aug. 9, 2005

(54) DEVICES AND METHODS FOR APPLYING KNOWN RESISTANCE LOADS AND MEASURING INTERNAL ANGLES OF GYRATION IN GYRATORY COMPACTORS

(75) Inventors: Roger A. Pyle, Clarion, PA (US); E. Frank Dalton, Mercer, PA (US)

(73) Assignee: Pine Instrument Company, Grove City, PA (US)

( * ) Notice: Subject to any disclaimer, the term of this patent is extended or adjusted under 35 U.S.C. 154(b) by 0 days.

(21) Appl. No.: 10/721,151

(22) Filed: Nov. 24, 2003

(65) Prior Publication Data

US 2004/0123685 A1 Jul. 1, 2004

Related U.S. Application Data

(63) Continuation-in-part of application No. 10/273,864, filed on Oct. 18, 2002.
(60) Provisional application No. 60/438,689, filed on Jan. 8, 2003.

(51) Int. Cl.$^7$ ................................................ G01N 3/08
(52) U.S. Cl. ........................................................ 73/813
(58) Field of Search ............................. 33/534; 73/813, 73/815, 816, 817, 819, 821, 825; 425/169, 171, 411, 415, 429

(56) References Cited

U.S. PATENT DOCUMENTS

| | | | |
|---|---|---|---|
| 2,972,249 A | 11/1961 | McRae et al. | |
| 3,461,717 A | 8/1969 | Dunlap et al. | |
| 3,478,572 A | 11/1969 | McRae | |

(Continued)

FOREIGN PATENT DOCUMENTS

EP 1 348 942 A2 1/2003

OTHER PUBLICATIONS

Test Quip, "Operating Instructions for the Dynamic Angle Validation Kit (DAV) for Superpave Gyratory Compactors", TestQuip Model DAV1, pp. 1–40, no date.
Dalton, Frank, "Gyratory Compaction, The Significance of the Internal Angle of Gyration", pp. 1–45, no date.
NCAT, "Evaluation of the Superpave Gyratory Compactor's Internal Gyration Angle in Alabama", pp. 1–31, no date.

(Continued)

Primary Examiner—Robert Raevis
(74) Attorney, Agent, or Firm—Roetzel & Andress (57) ABSTRACT

Devices and methods for providing a known resistance load and measuring an internal gyration angle of a mold in a gyratory compactor. A device in one form has a cylindrical body with protrusions through which a known resistance force is applied by the gyratory compactor, and probes which extend from the body to measure an internal angle of gyration of a mold within a gyratory compactor. The device is placed into a cylindrical mold which is placed into a gyratory compactor. Mold end plates may or may not be required depending on the gyratory compactor configuration and construction of the device body. As the mold is tilted on its axis to an operative gyration angle, the protrusions on each end of the body apply a moment force to the mold which produces a known resistance force on the gyratory compactor frame. Measurement of an internal angle of gyration is made while the resistance force is applied to the compactor frame and while the gyratory compactor gyrates the mold. The apparatus is then removed from the mold and the measured angle is obtained by connection to an external computer or directly read from the device. A display may be built into the body of the device to display the result directly. The components of the device inside the cylindrical body may be alternately arranged so that the angle measurement probes extend from the top or bottom or side wall of the cylindrical body. Use of an internal loading device in combination with an internal gyration angle measurement device is also disclosed. Use of an internal loading device in a gyratory compactor which is instrumented to measure an internal gyration angle external of the mold is also disclosed.

12 Claims, 6 Drawing Sheets

U.S. PATENT DOCUMENTS

| | | | |
|---|---|---|---|
| 3,640,127 | A | 2/1972 | Meissner |
| 3,881,346 | A | 5/1975 | Scheucher |
| 4,087,918 | A | 5/1978 | Schmid et al. |
| 4,452,065 | A | 6/1984 | Minter |
| 4,794,799 | A | 1/1989 | Paakkinen |
| 4,887,343 | A | 12/1989 | Ohishi |
| 4,930,346 | A | 6/1990 | Paakkinen et al. |
| 4,942,768 | A | 7/1990 | McRae |
| 5,036,709 | A | 8/1991 | McRae |
| 5,275,056 | A | 1/1994 | Hamilton et al. |
| 5,323,655 | A | 6/1994 | Eagan et al. |
| 5,456,118 | A | 10/1995 | Hines et al. |
| 5,606,133 | A | 2/1997 | Hines et al. |
| 5,698,789 | A | 12/1997 | Lainio et al. |
| 5,817,946 | A | 10/1998 | Brovold |
| 5,824,913 | A | 10/1998 | Pyle |
| 5,911,164 | A | 6/1999 | McRae |
| 5,936,398 | A | 8/1999 | Bellefuille |
| 5,939,642 | A | 8/1999 | King et al. |
| 6,026,692 | A | 2/2000 | Brovold |
| 6,205,864 | B1 | 3/2001 | Vialletel et al. |
| 6,477,783 | B1 | 11/2002 | Harman et al. |
| 2001/0049969 | A1 | 12/2001 | Bahia et al. |
| 2003/0089178 | A1 | 5/2003 | Paakkinen |
| 2003/0192384 | A1 | 10/2003 | Vema |

OTHER PUBLICATIONS

Pine Instrument, "Investigation of FHWA SGC AVK #3 Guide Rod Play", Sep. 27, 2000, pp. 1–8.

"Pressure Response Indicator HM–855", Last viewed on Oct. 17, 2003, p. 1, Gilson Company, Inc., http://www.globalgilson.com/sections/product/index.asp?pr_id=14171.

Guler, Murat, et al., "Development of a Device for Measuring Shear Resistance of HMA in the Gyratory Compactor", pp. 1–24, Paper No. 00–1318, The Asphalt Research Group.

"Gyratory Asphalt Mixture Design Gyratory Compactor Calibration", Apr. 4, 2001, pp. 1–2.

Raw Data from Recent Field Trials Using the Superpave Gyratory Compactor Dynamic Angle Validator (DAV), prepared for the Superpave ETG Meeting, Tempe, Arizona, Apr. 2–4, 2001.

Report 2001–01 Application of Internal Angle Verification to Obtain Equivalent Results from Various SGC Models, Pine Instrument Company, Aug. 23, 2001, pp. 1–9.

"Report 2000–03 Investigation of Pine Superpave Gyratory Compactors Using the FHWA Angle Validation Kit", Pine Instrument Company, Dec. 29, 2000, pp. 1–9.

"Report 2000–02 Observations of SGC End Plate Deflection Using the FHWA Angle Validation Kit", Pine Instrument Company, Oct. 11, 2000, pp. 1–11.

Al–Khateeb, Ghazi, et al., "Target and Tolerance Study for the Angle of Gyration used in the Superpave Gyratory Compactor (SGC)", http://www.tfhrc.gov/pavement/asphalt/labs/mixtures/target.htm, Aug. 22, 2002, pp. 1–16.

Superpave Gyratory Validation Kit Manufacturer's Meeting, Aug. 1931, pp. 1–7.

"Consideration of Mold Temperature When Measuring the Angle of Gyration on the Troxler Model 4140", Oct. 2001, pp. 1–6.

"Measuring the Angle of Gyration on the Troxler Superpave Gyratory Compactor—SGC Using an Internal Angle Measuring Device", pp. 1–4.

"Troxler's Superpave Gyratory Compactor Operational Specifications", Feb. 2001, pp. 1–5.

"Investigating Measurable Gmb Differences Among Gyratory Compacted Specimens", May 2001, pp. 1–9.

"FGWA Angle Kit Studies at Pine", pp. 1–14.

"Economic Impact Refining the Dynamic Internal Angle of the Superpave Gyratory Compactor", Jan. 29, 2003, pp. 1–10.

Buchanan, Shane, M., et al., "Effect of Superpave Gyratory Compactor Type on Compacted Hot Mix Asphalt (HMA) Density", Jan. 7–11, 2001, pp. 1–23.

Pine Instrument Company, Report 2000–01, "Superpave Gyratory Compactors—Angle Sensitivity", Mar. 30, 2000, pp. 1–9.

Schiebel, Bill, "CDOT and Colorado Paving Industry's Action Plan to Address Recently Documented Issue with Compaction Angle . . . ", Apr. 19, 2002, pp. 1–16.

"Model 3191 True Mold Angle Device for the Model 4141 Gyratory Compactor", pp. 1–16.

"Model 3190 True Mold Angle Device for the Model 4140 Gyratory Compactor", pp. 1–20.

International Search Report.

DEVICES AND METHODS FOR APPLYING KNOWN RESISTANCE LOADS AND MEASURING INTERNAL ANGLES OF GYRATION IN GYRATORY COMPACTORS

RELATED APPLICATIONS

This application is a conversion of U.S. Provisional Application Ser. No. 60/438,689, filed Jan. 8, 2003, and a continuation-in-part of U.S. application Ser. No. 10/273,864, filed Oct. 18, 2002.

FIELD OF THE INVENTION

This invention relates, in general, to the measurement of an angle of gyration in material testing equipment such as gyratory compactors, and to devices which simulate forces of materials which are tested by gyratory compactors.

BACKGROUND OF THE INVENTION

Gyratory compactors, including the SUPERPAVE Gyratory Compactors (SGC) developed in response to the Federal Highway Administration's SHRP research program, have proven to be a useful tool in the design and quality assurance programs for Hot Mix Asphalt (HMA) products. The SGC applies a constant consolidation pressure onto a material specimen, such as HMA, contained within a cylindrical mold of specified dimensions. The specimen is confined within the mold typically between two end plates which fit within the mold. While the consolidation pressure is applied, the cylindrical mold is tilted on its axis (i.e., one end of the axis displaced while the other end is held fixed) to a precise angle, known in the art as the angle of gyration, or gyration angle. The tilted axis is then gyrated around an axis perpendicular to the mold end plates, which may also be the axis along which the consolidation pressure is applied, i.e., the axis of consolidation or compaction. The gyration of the mold is performed at a specified rate.

Studies have shown that the angle of gyration, as determined by the degree of tilt of the mold axis from the axis perpendicular to the mold end plates, plays a key role in determining the amount of compaction a material specimen, such as HMA, experiences during gyration. The primary method used to measure the angle of gyration is to measure the angle between an external surface of the mold cylinder with reference to a stationary external reference, such as a member of the surrounding frame of the gyratory compactor. However, such measurement of an external angle of gyration, in addition to being subject to variances introduced by deflection of the machine frame, does not account for movement of the mold end plates within the mold resulting from the reaction forces of the material specimen in the mold (including shear forces between the material and the mold wall) which are transferred to the machine frame. It is the internal angle between the mold cylinder and the compaction/planar surfaces of the mold end plates which contact the specimen that determines the amount of compaction effort imparted to the specimen. This is referred to as the "internal angle of gyration" or "internal gyration angle"; the angle formed between the internal mold wall and the mold end plates during compaction. When two mold end plates are used in the mold, one at each end of the material specimen, the internal gyration angle can be measured with respect to each end plate. With the mold vertically oriented in an SGC and a mold end plate at the top and bottom of the specimen, these internal angle measurements are generally referred to as the top (internal) angle and the bottom (internal) angle.

U.S. Pat. No. 6,477,783 (the '783 patent) describes a device that fits inside the SGC mold along with a material specimen, such as an HMA, which is placed on top of the device while the SGC is operated. A flat end of the device is placed flush against the bottom mold plate, and an HMA specimen is placed on top of the device. Probes extend out of a side wall of the device to contact the inside wall of the mold. The device disclosed in the '783 patent is operable only with an HMA material specimen in the mold on top of the device, in order to apply the material-induced loads to the SGC frame so as to measure the internal angle of gyration under what is assumed to be realistic, material-based conditions. However, the molds used in many existing SGC models do not have sufficient volume to hold a typical size material specimen and the internal angle measuring device described by the '783 patent. The forces acting on the gyratory compactor frame are related to the material stiffness as well as to the amount of material being compacted. The inability to use typical sized specimens with the device of the '783 patent in some SGC models (or the use of undersized specimens) necessitates use of a complex procedure to accurately predict the angle with a full sized specimen. To overcome this shortcoming, it is necessary to take multiple measurements (e.g., as many as seven or more) with specimens of different masses compacted with the angle measurement device of the '783 patent, and then perform an extrapolation calculation to predict what the internal angle of gyration is with a full size specimen. Because the mold must cleaned, pre-heated and loaded with the device, and the material must be pre-heated and loaded into the mold on top of the device, the repetition of this process seven or more times can consume nearly an entire work day just to measure the internal gyration angle of a single gyratory compactor.

HMA material specimens have varying stiffness properties that can be difficult to characterize accurately, creating a situation of an unknown force being applied while the measurement is made. Each SGC model has a unique frame stiffness resulting in a characteristic different frame deflection during operation. Frame deflection may cause different angles of gyration for HMA specimens of different stiffnesses in SGC models with relatively more flexible frames. It is important to have known forces similar to that of the material typically compacted to overcome this problem. Furthermore, because the internal gyration angle measurement device of the '783 patent is used exclusively with a material sample in the mold, the compaction ram and its support structure is not in a position similar to that of normal operation, creating possible changes in frame stiffness characteristics due to the extension of the ram, which further alters the test results.

As noted above, the angle of gyration must be known with great accuracy. To make an accurate measurement, the apparatus, molds, mold end plates, and the SGC apparatus must be very clean. The device and method described in the '783 patent requires the use of HMA consisting of aggregates of various sizes mixed with asphalt binder, a tar-like substance, which makes debris a significant factor in the accuracy of this angle measurement. Also, HMA specimens are typically compacted at 150° C., making the procedure difficult and creating operator safety concerns as well as problems associated with overheating the measurement device. The extreme care necessary to minimize the effect of temperature on the measurements requires a cooling period for the instrument between measurements, adding still more time to the lengthy angle measurement, extrapolation and calibration process. The horizontal probes of the '783 patent device are aligned vertically to interface with the curved inner surface of the mold wall while the flat base contacts a mold endplate. Dirt or debris between the mold end plates and the '783 patent device can significantly effect the accuracy of the measurement. Because of the need for extreme accuracy, close attention must be used to minimize the effect of dirt or debris in the measurement.

It is therefore desirable to obtain a very accurate measurement of this internal angle of gyration under actual material loads. Even more preferable would be to obtain highly accurate measurement of the internal angle of gyration under conditions similar to those occurring during compaction of the sample material, without having material actually present in the mold. This would be particularly advantageous for angle calibration of gyratory compactors for use with HMA, to avoid pre-heating of the mold and material, and repeated loading and unloading of the mold with HMA to obtain an accurate measurement of the internal gyration angle.

SUMMARY OF THE INVENTION

The present invention overcomes the shortcomings of the apparatus disclosed in U.S. Pat. No. 6,477,783 and other angle measurement devices, by applying a known resistance force to an SGC frame without a sample material in the mold, while simultaneously measuring an internal angle of gyration. In a preferred embodiment, a body of the device is approximately the height of a typical HMA material specimen, and therefore can be used universally with all SGC models without requiring the use of a complex extrapolation procedure utilizing multiple specimen masses. The device can also apply different known resistance forces to establish the frame stiffness characteristic for a particular SGC model. Measurements can be made at room temperature to improve operator safety and convenience or they may be made with the mold and end plate at normal compaction temperature which is typically 150° C. Sample material is not required in the mold, reducing the amount of preparation required to perform the angle measurement. Angle measurement probes are oriented to engage a flat surface of a mold end plate while the cylindrical body follows the movement of the mold. This is an improvement over prior art as the probes only contact a small area of the mold end plate, thereby reducing the potential for debris to effect the measurement.

The invention includes the concept of placing in a mold in a gyratory compactor an internal gyration angle measurement device and a separate loading device. In one form of the invention, there is provided a system for applying a load and measuring an internal angle of gyration in a mold adapted for use in a gyratory compactor, the mold having a wall and mold plates which fit within the mold wall, the system including: an internal gyration angle measurement device which fits within the mold wall and in planar contact with a first mold plate, the internal angle measurement device having at least one probe which contacts the mold wall; a second mold plate in planar contact with the internal gyration angle measurement device on a side of the internal gyration angle measurement device opposite to the first mold plate; a loading device within the mold and in contact with the second mold plate, and in contact with a third mold plate on a side of the loading device opposite to the second mold plate.

In accordance with another aspect of the invention, there is provided a device for applying a known resistance force and measuring an internal angle of gyration of a mold in a gyratory compactor, the device including a body configured to fit within a mold suitable for use in a gyratory compactor, the body having a first end and a second end and a side wall which extends between the first and second ends, the first and second ends extending laterally beyond the side wall; a protrusion which extends from the first end, and a protrusion which extends from the second end, each protrusion configured to provide a contact with a mold end plate, the body providing resistance to a force applied to the body by contact with one of the protrusions; an assembly within the body for measuring an internal angle of gyration, the assembly including a guide block, guide block probes in the guide block which extend outward from the side wall of the body, a guide rod for holding a reference probe to extend through one of the first or second ends of the body, a slide block attached to the guide rod, and a linear sensor probe mounted to the slide block to extend through one of the first or second ends of the body.

In accordance with another aspect of the invention, there is provided a system for applying a load and measuring an internal angle of gyration in a mold adapted for use in a gyratory compactor, the mold having a wall and mold plates which fit within the mold wall, the system having an internal gyration angle measurement device which fits within the mold wall and in planar contact with a first mold plate, the internal angle measurement device having at least one probe which contacts the mold wall; a second mold plate in planar contact with the internal gyration angle measurement device on a side of the internal gyration angle measurement device opposite to the first mold plate, and a loading device within the mold and in contact with the second mold plate.

A method of the invention of measuring an internal gyration angle in a mold in a gyratory compactor includes the steps of positioning an internal gyration angle measurement device in a mold between two mold plates, the internal gyration angle measurement device having a body with planar ends which are positioned in planar contact with the mold plates; positioning a loading device in the mold in contact with one of the two mold plates in contact with the internal gyration angle measurement device; applying a force to the loading device as the mold is gyrated in a gyratory compactor, and obtaining a measurement of an internal gyration angle from the internal gyration angle measurement device measured while the force is applied to the loading device and while the mold is gyrated.

These and other novel concepts and methods are herein described in detail with reference to the accompanying Figures.

DETAILED DESCRIPTION OF PREFERRED AND ALTERNATE EMBODIMENTS

FIGS. 1–5 illustrate a first embodiment of an internal loading and internal gyration angle measurement device of the invention, indicated generally at 10. The device 10 in this particular form has a generally cylindrical body 20 which is generally configured to fit within a cylindrical mold of the type used in a gyratory compactor, such as a Superpave gyratory compactor. The body 20 of the device 10 can of course take different shapes and forms in relation to the mold in which it is to be used as described. In this embodiment, designed for use in a cylindrical mold M, as shown for example in FIG. 5, of the type used in Superpave gyratory compactors, the generally cylindrical body 20 is defined by circular end caps 22 and 24 with a wall 30 which extends between the end caps 22 and 24. Although shown in cylindrical form, the form of the wall 30 is not necessarily dictated by the form of the mold M, however in this instance the outside diameter of the wall 30 of the body is just slightly less than the inside diameter of the mold M. The circular end caps 22 and 24 are configured to closely match the inside diameter of the mold M so that the body 20 of the device moves in axial alignment with the mold M as the mold is gyrated at a gyration angle.

When installed in a gyratory compactor the mold M is gyrated, i.e., one end of an axis, such as the longitudinal axis, of the mold cylinder is moved in a circular path while the opposite end of the same axis is held at a fixed point, or some point along the axis of the mold is held while the ends of the mold are gyrated. The mold M is thus gyrated by any suitable mechanism, such as those known in the art, including those described in the patents cited and disclosed in connection with this patent. In general, mold gyration mechanisms include those which engage a portion of the mold cylinder, such as the mold wall or a flange which extends from or surrounds the mold cylinder, in order to move the mold in a gyrating or orbiting motion, and those which otherwise displace the mold cylinder from an axis of compression or travel of a ram inserted into the mold, by a mechanism which includes a rotationally driven eccentric to impart a gyratory motion to the mold. Other gyratory mechanisms move the mold end plates while holding the mold cylinder stationary to create the gyratory action on material in the mold. All such mechanisms, including all gyratory compactors of the prior art are included within the meanings of the terms "gyratory compactor" and "mold gyration mechanism" and variants as used herein.

Figure 5:
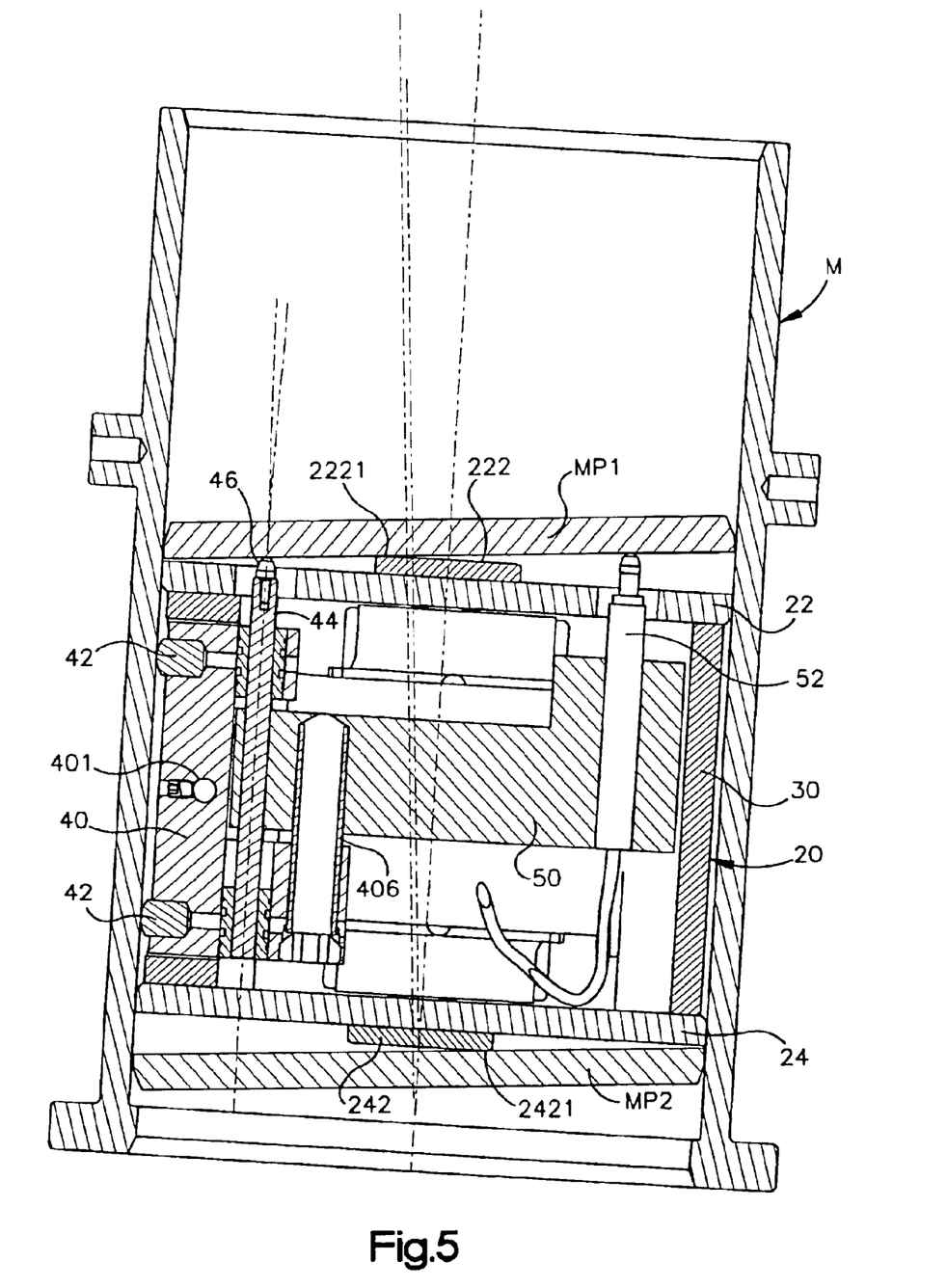
FIG. 5 is a cross-sectional view of the device of FIG. 1, shown in position in a cylindrical mold of the type used in gyratory compactors, and with mold endplates in the mold.

Each end cap 22 and 24 has a corresponding protrusion, 222 and 242, which projects or extends from the outer plane of the respective end cap. In the form as shown, the protrusions 222, 242 are disk shaped and located at the radial center of the respective end. Each protrusion 222, 242 has a contact edge 2221 and 2421 which contacts an opposing mold end plate, MP1, MP2, as shown in FIG. 5. The mold end plates, MP1 and MP2, are plates which fit within the mold with sufficient clearance to be positionable at angles relative to a vertical axis of the mold, as shown in FIG. 5. Because the protrusions 222, 242 are circular, when the mold end plates MP1 and MP2 are angled relative to the plane of the end caps 22 and 24 (or when the mold M with the device 10 therein is angled relative to the plane of the mold end plates MP1, MP2) the protrusions 222, 224 contact the respective mold end plates MP1, MP2 at the contact edges 2221, 2421, as shown in FIG. 5. Although the actual physical area of contact between the contact edges 2221, 2421 and the respective mold end plates MP1, MP2 may be greater than a literal point, the interface between these two components is referred to herein as the "contact", "contact edge" or "contact point".

Contained within the body 20 is instrumentation which is operative to measure the internal angle of gyration within a mold M, with reference to the interior of the mold M and either of the mold end plates MP1, MP2, or both. FIGS. 1–5 illustrate an embodiment which includes a guide block 40 positioned proximate to and within an opening 32 in wall 30. One or more guide block probes 42 are mounted within the guide block to extend outward from wall 30 for contact with the interior of a mold M, as shown in FIG. 5. The guide block 40 is pivotably mounted, for example at pivot 401, to the device body 20 and spring biased by springs 402 to force the guide block probes 42 into contact with the mold. The guide block probes 42 can be mounted in other ways within the device body which may not require the guide block 40. Attached to or extending from the guide block 40 is a guide rod 44, mounted to the guide block 40 with linear bearings to allow the guide rod 44 to slide within the guide block 40. The guide rod 44 is spring biased, by spring 406, against a mold end plate, MP1 or MP2. The guide rod 44 is oriented generally orthogonal to the guide block probes 42, to extend through one of the end caps 22, 24 toward one of the mold end plates, in this case toward mold end plate MP1. A reference probe 46 is positioned within the guide rod 44, e.g. by threaded engagement or machined as part of the guide rod 44, to extend through end cap 22 to contact the mold plate. Alternatively, the reference probe 46 can protrude from or extend through end cap 24 of the body 20 for contact with mold plate MP2.

Also internal to the device body 20, a slide block 50 is attached directly to the guide rod 44 to move with the guide rod as it slides within the linear bearings. An additional set of bearings prevents the slide block 50 from rotating around the guide rod 44. A linear position sensor probe 52, such as preferably a linear variable differential transformer (LVDT) or similar position measuring probe, is mounted to the slide block 50, with the probe 52 and probe tip 521 spring biased toward the respective mold end plate. The linear position sensor probe 52 is also spring biased to maintain contact with the corresponding mold end plate during operation, and can alternatively be positioned to extend through either end cap 22 or 24 of the cylindrical body 20.

As the device 20 is placed into the cylindrical mold (with mold end plate MP1 at one end of the device facing end cap 22 or 24, and mold end plate MP2 at an opposite end of the device facing the other end cap), the guide block 40 is compressed against its mounting spring to force the guide block probes 42 into contact with the interior of the wall of mold M. This provides a reference and confirmation of the co-axial position of the device body 20 with the mold M. The reference probe 46 then contacts a mold end plate, and the linear position sensor probe 52 also contacts a mold end plate. The reference probe 46, being located proximate to the guide block probes 42 and oriented ninety degrees thereto, and being mounted in the slide block 50 with the linear position sensor probe 52, provides a reference measurement of the position of the mold end plate relative to the device body 20, and more particularly with reference to the plane of the end cap 22 (or end cap 24 in the case where reference probe 46 is positioned to extend therethrough). Linear position measurements by the linear position sensor probe 52 are then made with reference to the inputs of probes 42 and 46, and these measurements input to an appropriately programmed circuit (preferably residing on a microchip in circuitry contained within the device body) which calculates an internal angle of gyration from the sensed position(s) of the mold end plates relative to the interior of the mold.

Figure 6:
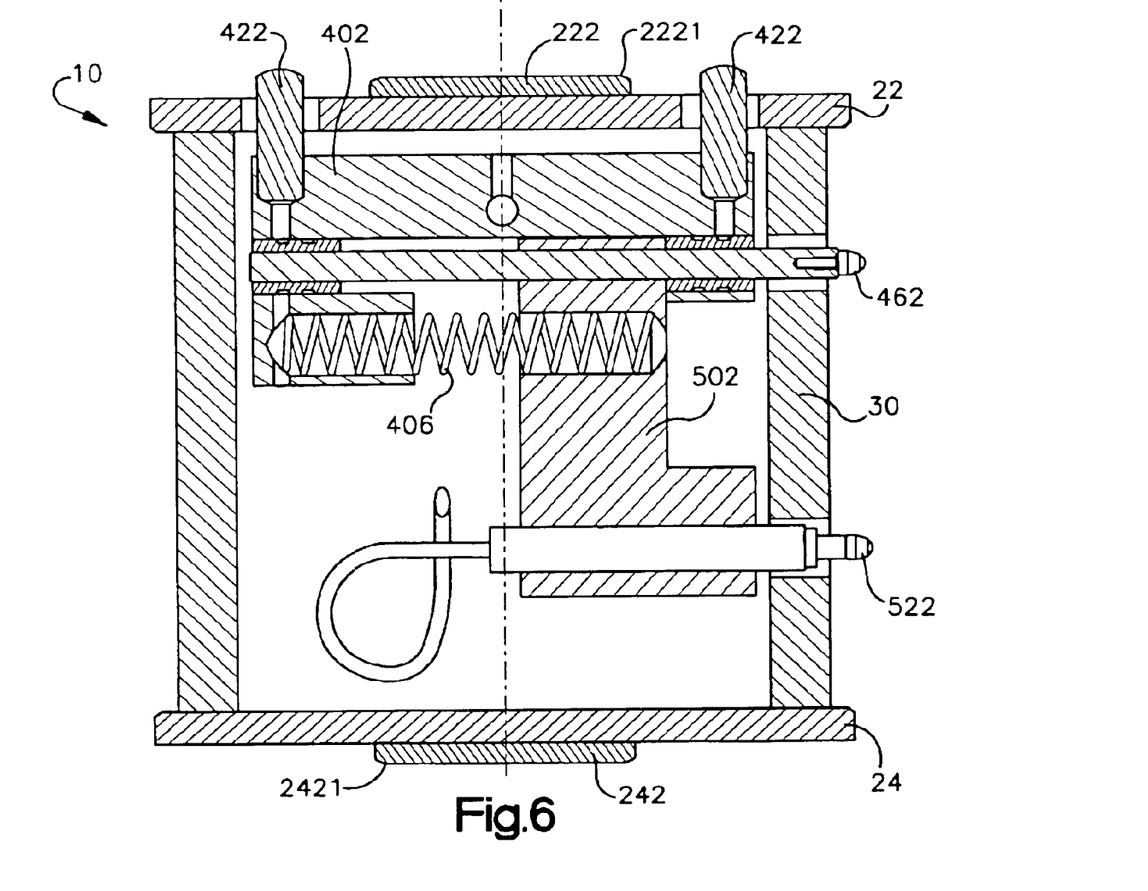
FIG. 6 is a cross-sectional view of an alternate embodiment of a resistance loading and internal gyration angle measurement device of the invention.

As shown in FIG. 6, the invention further includes an alternate embodiment which utilizes multiple reference and linear position sensor probes by, for example, use of an alternately positioned or oriented guide block 402 and an accompanying slide block 502 inside the body 20. In this particular orientation of the internal angle measurement instrumentation, the guide block sensor probes 422, mounted in guide block 402, extend through end cap 22. The reference probe 462 extends through the wall 30 of the device body 20, as does the linear position sensor probe 522. The slide block 502 is spring biased in a direction parallel to the end caps 22, 24. Alternatively, a single guide block may be combined with two slide blocks spring biased in opposite directions relative to the device end caps, with each slide block having a reference probe and a linear position sensor probe which extends through the corresponding end cap for contact with the corresponding mold end plate. Embodiments with a second linear position sensor probe would require a second signal conditioner.

Figure 1:
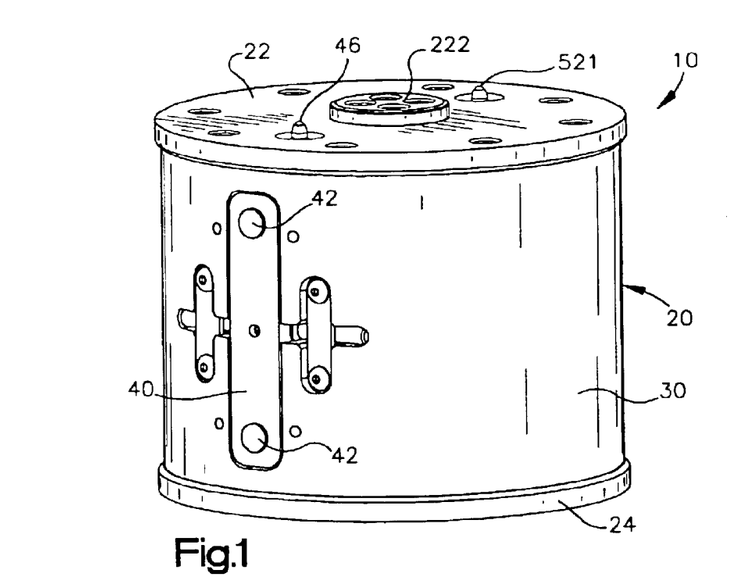
FIG. 1 is a perspective view of a representative embodiment of a resistance loading and gyration angle measurement device of the invention.
Figure 2:
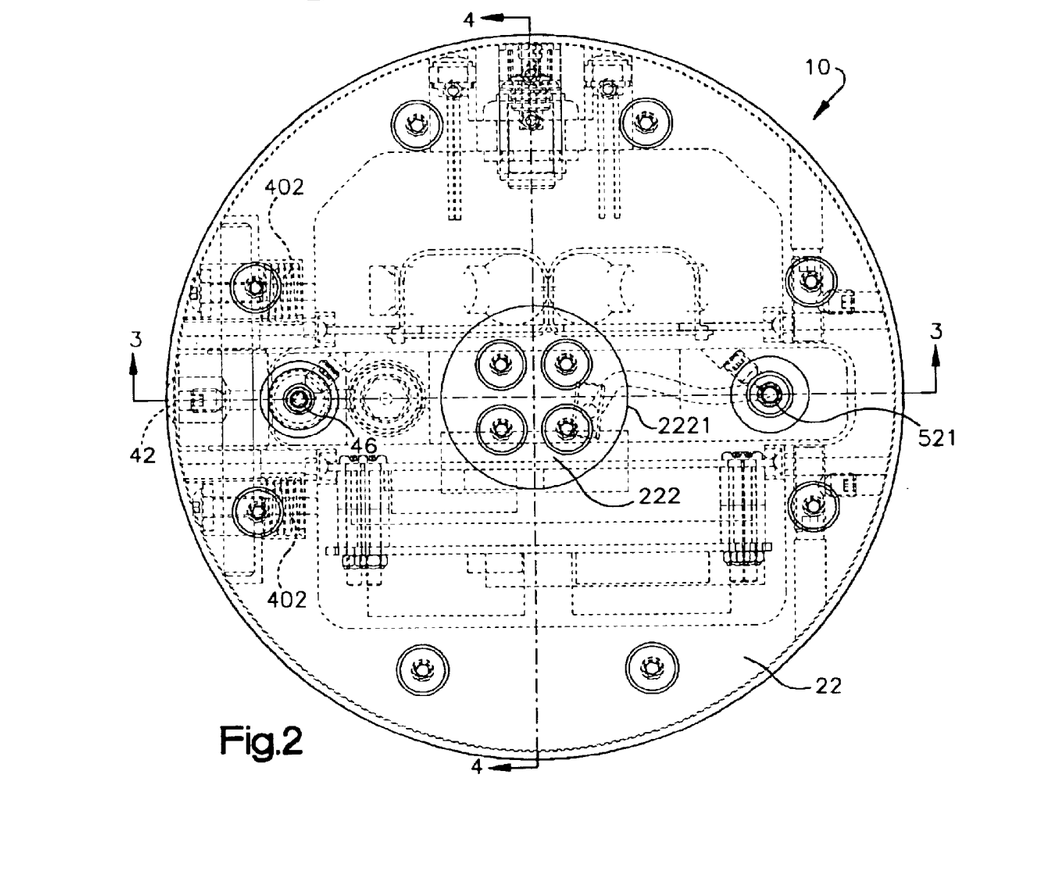
FIG. 2 is a top view of the device of FIG. 1 with certain internal components represented with dashed lines.
Figure 3:
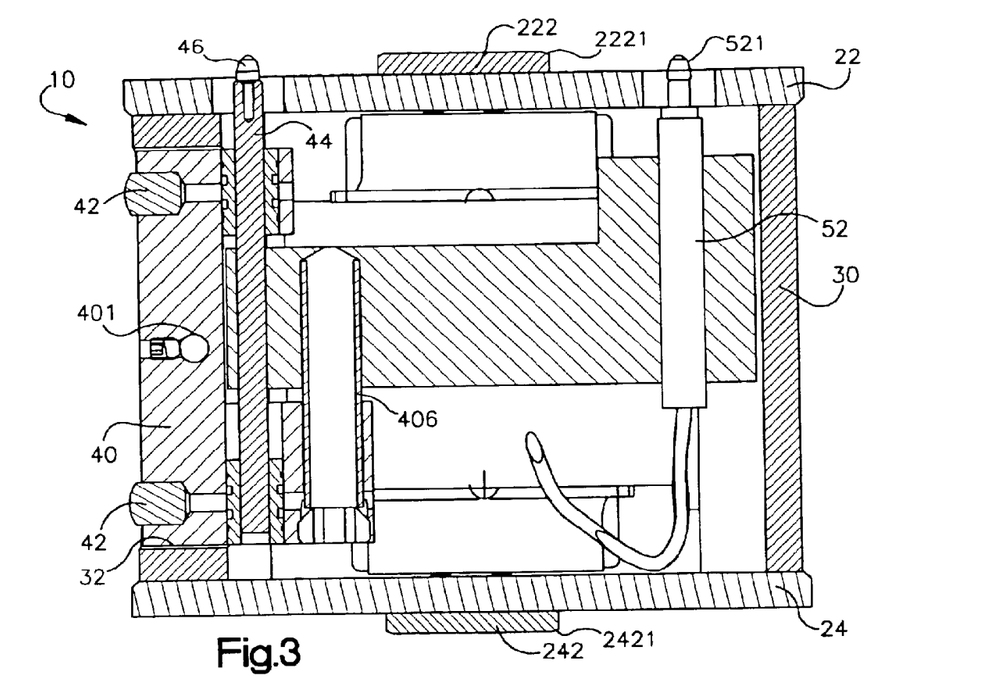
FIG. 3 is a cross-sectional view of the apparatus of FIG. 1 in the direction indicated on FIG. 2.
Figure 4:
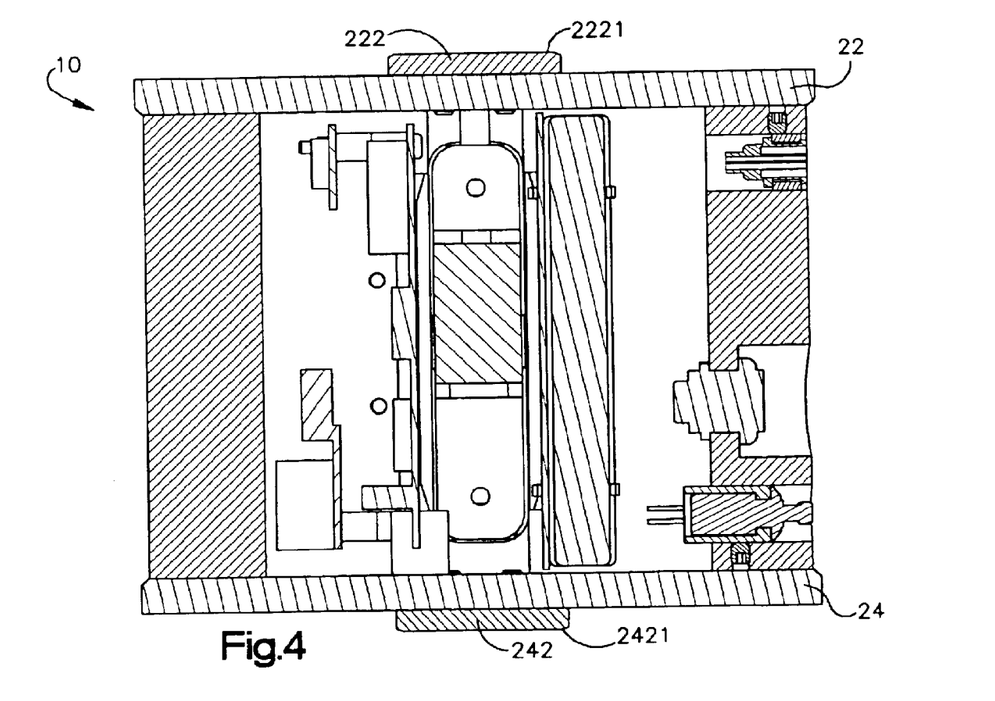
FIG. 4 is a cross-sectional view of the device of FIG. 1 in the direction indicated on FIG. 2.

As shown in FIG. 5, the device 10 is placed within a mold M between mold end plates MP1 and MP2. The mold M is then loaded into a SGC and the SGC operated in a normal manner. A compaction ram of the SGC applies a consolidation pressure to the device 10 through one of the mold end plates MP1 or MP2, and the mold M is displaced to an angle of gyration, as shown in FIG. 4. Once at a gyration angle, the contact edges 2221, 2421 of protrusions 222, 242 make contact with the respective mold plates to apply a moment force to the mold and the SGC machine similar to the forces created by an actual HMA specimen in the mold. As noted, the forces acting on the SGC frame causes a deflection in the frame. Because the device 10 creates a precisely known load which is a product of the forces used to apply the consolidation pressure and the diameter of the end protrusions 222, 242, the SGC frame deflection and an angle of gyration is determined from precisely known loading conditions. By applying these forces while simultaneously measuring an internal angle of gyration with the SGC loaded in approximately the same manner as when compacting a typical HMA specimen, the invention is able to accurately measure an internal angle of gyration under consolidation or compaction loading without a material specimen present in the mold.

Of course the size and diameter of the end protrusions 222, 242 and corresponding locations of the contact edges 2221, 2421 dictate the force vectors applied to the mold and SGC. Accordingly, the diameter of the end protrusions can be altered by exchange of different sized protrusion by mechanical detachment/attachment to the end caps 22, 24 and/or the force applied to the device by the SGC compaction ram can be varied to obtain different levels of loading, again without the presence of HMA or other material in the mold. A smaller diameter protrusion results in a smaller moment load simulating a weak HMA material, while a larger diameter results in a larger moment simulating a strong HMA material. Generally, a smaller compaction force on a given diameter protrusion will also reduce the moment load while a larger force will increase the load. In this manner, a known reaction force of the desired level can be applied to the SGC frame to simulate the desired load condition during the angle measurement. This is an important aspect of the device as each SGC model has its own frame stiffness characteristics. A stiff SGC frame will hold a substantially constant angle of gyration at various moment loads, while a less stiff SGC frame will show a variance in the angle of gyration for different reaction forces. Because of the different SGC frame stiffness, it is important to apply a known load to the SGC while measuring the angle of gyration thus this invention is advantageous over existing techniques which require the use of materials with an unknown stiffness. It is important to characterize a SGC frame so that the changes in the angle of gyration resulting from different HMA stiffness can be quantified. The end protrusions 222, 242 can be made detachable and interchangeable to ease the use of different diameters, or may be made as an integral part of the cylindrical body.

The device 10 is preferably self-contained with a portable power source such as a battery and data acquisition electronics. The device can be connected to an external computer once the measurement is complete to retrieve and display the measured angle, or the device may include a display on the body 20, for example by incorporation into wall 30, to directly display the measured angle without the aid of a separate computer or display device. Or, the device 10 can be configured with appropriate hardware and software for wireless transmission of angle measurement data to a receiver external to the device and the SGC.

Calibration of the device is accomplished through the use a machined block with multiple known angles. The device is placed into the block against the reference surface for each known angle and the output of the device is matched to the known value of the machined block. This provides a traceable calibration to a known standard.

Figure 7A:
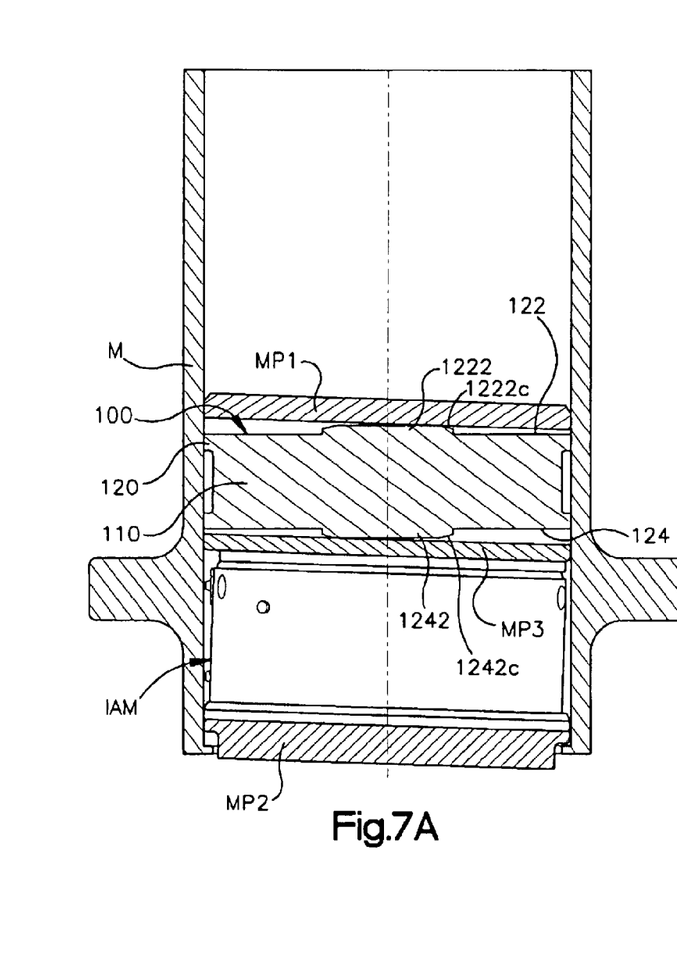
FIGS. 7A and 7B are cross-sectional views of an internal loading device of the invention shown in position in a mold with an internal gyration angle measurement device.
Figure 7B:
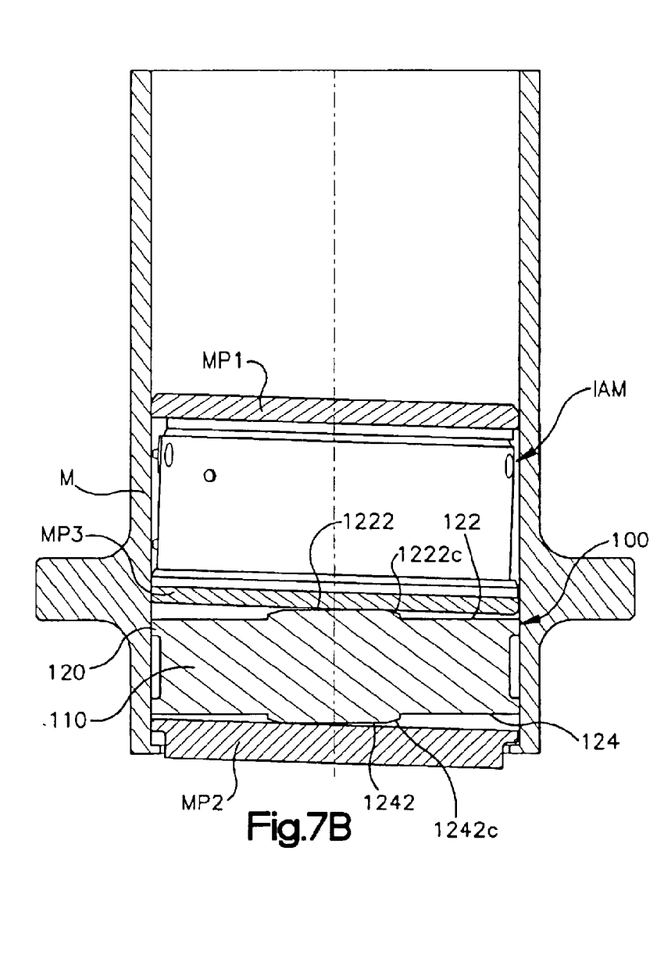

FIGS. 7A and 7B illustrate a non-instrumented internal loading device, indicated generally at 100, which can be used to simulate the forces of material specimens within a mold M. As illustrated, the device 100 is used in accordance with the invention in combination with an internal angle measurement device IAM which fits within the mold M. The non-instrumented internal loading device 100 has a body 110 generally configured to fit within a mold, such a cylindrical mold M, and can be made with one or more flanges 120 which extend outward from the body 110, for example radially outward from the body, to closely match the internal diameter of the mold M. Alternatively, the body 110 can be made with an outer diameter which closely matches the internal diameter of the mold M. Protrusions 1222, 1242 extend from opposing ends 122, 124 of the body 110, each of the protrusions having a contact edge 1222c, 1242c which contact the corresponding mold plates MP1, M3 when the device is positioned between the mold plates within a mold, as shown. Because the contact edges 1222c, 1242c are radially offset or eccentric from the axis of the body of the device 100 (which is coaxial with the longitudinal axis of the mold), a moment is applied to the gyratory compactor in which the mold is installed which is comparable to that created by shear resistance of material such as HMA in a mold when gyrated.

In order to measure the internal angle of gyration while the SGC is under the simulated material load, the device 100, between mold plates MP1 and MP3, is placed in the mold M on top of an internal angle measurement device, such as device IAM of the type for example described in U.S. Pat. No. 6,477,783 as shown in FIG. 7A. The mold end plate at the bottom, MP2, is positioned under the internal angle measurement device. An advantage of this combination of components within the mold, in addition to not requiring a material specimen in the mold, is that the body of the internal angle measurement device does not have to be configured with moment-inducing protrusions, and does not bear the mechanical stress of the compaction force of the SGC. Compaction forces are transferred through the measurement device to the mold end plate MP2 and to the SGC frame. The intermediate mold plate MP3, and the underlying mold plate MP2, protects the internal gyration angle measurement device from damage within the mold. However, the mold plates can be dispensed with if the housing of the internal gyration angle measurement device is built strongly enough to bear against the loading device under a compaction force. For example, the intermediate mold plate MP3 as shown in FIGS. 7A and 7B can be dispensed with when used with an internal angle measurement device with adequate housing strength. In the arrangement as shown with the internal gyration angle measurement device under the non-instrumented internal loading device 100 (FIG. 7A), the internal angle of gyration at the bottom of the mold is measured. To measure the internal gyration angle at the top of the mold, the assembly of the device 100, MP3 and the internal gyration angle measurement device (10 or IAM) can be inverted within the mold as shown in FIG. 7B. The mold plates may be independent pieces within the mold or attached to other components such as to a compaction ram or ram foot. As noted, the intermediate plate MP3 may not be required in either type arrangement depending upon the strength of the housing of the IAM.

Figure 8:
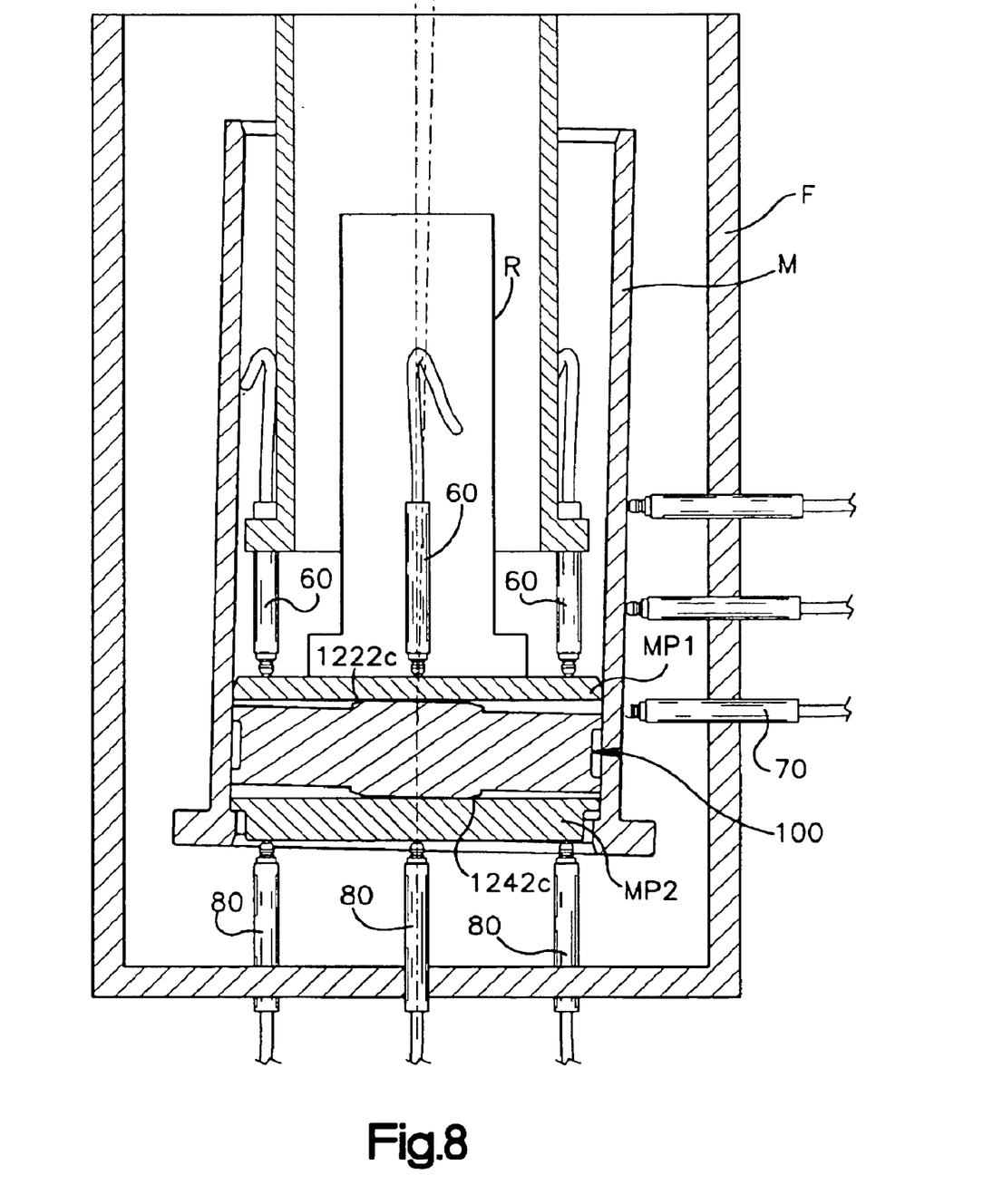
FIG. 8 is a cross-sectional view of a mold and surrounding frame of a gyratory compactor which is instrumented for measurement of an internal gyration angle, and with a resistance loading device in the mold.

The loading device 100 can also be used in accordance with the invention with a SGC which is instrumented with probes and sensors external to the mold M and mold end plates to measure an internal angle of gyration, as described in the co-pending application Ser. No. 10/273,864. As described therein, an array of sensors is provided external to the mold and mold end plates to determine a relative position of these components while the mold is gyrated, and from which positional data an internal gyration angle is calculated. Each of the sensors of the array may be intergrally mounted to the SGC for operative contact with the mold and mold end plates, whether by direct physical contact, such as linear variable differential transformer (LVDT) sensors, or optical sensors or the like. The sensors or sensor arrays are operative to determine position or orientation of machine components, such as a mold or mold end plates, to provide data from which an internal gyration angle can be determined. As shown in FIG. 8, the device 100 is positioned by itself in a mold M between mold end plates MP1 and MP2. As described in application Ser. No. 10/273,864, the gyratory compactor (SGC) in which the mold M is placed is instrumented with sensors in operative contact with the mold M and at least one or both of the mold end plates MP1, MP2, such as for example by contact with externally arranged probes 60, 70, 80 which measure the relative positions of the mold and end plates to thereby determine the internal gyration angle at one or both of the end plates. With the device 100 present in the mold and under the applied force of the compaction ram R, the device 100 transfers moment forces through contact points 1222c, 1224c to simulate the forces of a material specimen in the mold, thus providing simulated but accurate internal gyration angle measurements.

Although the invention has been shown and described with respect to certain preferred embodiments, certain variations and modifications may occur to those skilled in the art. For example, many different types of position sensors, including angular measuring sensors, may be substituted for the various probes and sensors described. Additional probes may be added to extend through the end caps of the body, and additional probes provided through both end caps to measure multiple angles simultaneously. The device may also be used to simulate the loading characteristics of materials other than asphalt and asphalt aggregates. All such variations and modifications of the device and its various components and methods of use are within the scope of the present invention as defined by the claims and equivalents thereto.

What is claimed as the invention is:

1. A system for applying a load and measuring an internal angle of gyration in a mold adapted for use in a gyratory compactor, the mold having a wall and first and second mold plates which fit within the mold, the system comprising:

an internal gyration angle measurement device which fits within the mold and in planar contact with a first mold plate which fits within the mold, the internal angle measurement device having at least one probe which contacts the mold wall;

a second mold plate in planar contact with the internal gyration angle measurement device on a side of the internal gyration angle measurement device opposite to the first mold plate, and a loading device within the mold and in contact with the second mold plate.

2. The system of claim 1 wherein the loading device contacts the second mold plate at one point, and contacts a third mold plate opposite to the second mold plate at one point.

3. The system of claim 1 wherein the first mold plate is positioned at or near a bottom of the mold, the second mold plate is positioned between the internal gyration angle measurement device and the loading device.

4. The system of claim 1 wherein the loading device is positioned above the internal gyration angle measurement device within the mold.

5. The system of claim 1 wherein the internal gyration angle measurement device is positioned above the loading device within the mold.

6. The system of claim 1 wherein the loading device is in single point contact with two mold plates in the mold, and the internal gyration angle measurement device is in planar contact with a mold plate.

7. A system for applying a load and measuring an internal angle of gyration in a mold used in a gyratory compactor, the system comprising:

an internal gyration angle measurement device which fits within the mold and which contacts a wall of the mold;

a loading device which fits within the mold, the loading device having a first protrusion which applies force to the internal gyration angle measurement device.

8. The system of claim 7 wherein the loading device is positioned on top of the internal gyration angle measurement device within the mold.

9. The system of claim 7 wherein the loading device is positioned underneath the internal gyration angle measurement device within the mold.

10. The system of claim 7 wherein the loading device has a second protrusion which is contacted by a compaction ram which is inserted into the mold.

11. The system of claim 7 wherein the loading device has a second protrusion which contacts a mold plate within the mold.

12. The system of claim 7 wherein the the internal gyration angle measurement device is contacted by a compaction ram which is inserted into the mold.

* * * * *